(12) United States Patent
Abadie et al.

(10) Patent No.: US 7,918,789 B2
(45) Date of Patent: Apr. 5, 2011

(54) LONGITUDINALLY-STEERABLE STRUCTURE AND ENDOSCOPE COMPRISING SAID STRUCTURE

(75) Inventors: Joel Abadie, Besancon (FR); Nicolas Chaillet, Bonnay (FR); Christian Lexcellent, Besancon (FR)

(73) Assignees: Centre National de la Recherche Scientifique, Paris Cedex (FR); Ecole Nationale Superieure de Mecanique et des Microtechniques, Besancon (FR)

( * ) Notice: Subject to any disclaimer, the term of this patent is extended or adjusted under 35 U.S.C. 154(b) by 1089 days.

(21) Appl. No.: 10/542,350

(22) PCT Filed: Jan. 15, 2004

(86) PCT No.: PCT/FR2004/000072
§ 371 (c)(1),
(2), (4) Date: Apr. 18, 2006

(87) PCT Pub. No.: WO2004/066831
PCT Pub. Date: Aug. 12, 2004

(65) Prior Publication Data
US 2006/0232669 A1    Oct. 19, 2006

(30) Foreign Application Priority Data
Jan. 15, 2003    (FR) ...................................... 03 00421

(51) Int. Cl.
*A61B 1/04*    (2006.01)

(52) U.S. Cl. ........................... 600/152; 600/151; 348/76
(58) Field of Classification Search .................. 600/143, 600/151, 152, 146; 60/527, 528; 318/117
See application file for complete search history.

(56) References Cited

U.S. PATENT DOCUMENTS 4,543,090 A * 9/1985 McCoy ...................... 604/95.05
5,588,295 A * 12/1996 Brotz .............................. 60/528

FOREIGN PATENT DOCUMENTS
JP        2000135288 A   *   5/2000

OTHER PUBLICATIONS

Abadie et al. "An integrated shape memory alloy micro-actuator controlled by thermoelectric effect." 2002. Sensors and Actuators A, vol. 99. pp. 297-303.*

* cited by examiner

*Primary Examiner* — Matthew J Kasztejna
(74) *Attorney, Agent, or Firm* — Bachman & LaPointe, P.C.

(57) ABSTRACT

The invention relates to a longitudinally-steerable structure, comprising essentially longitudinal actuators made from shape memory alloy, Peltier effect elements with N and P doping and electrical control device. The above is characterized in that the actuators are arranged in pairs in an antagonistic manner, each actuator being connected at the ends thereof with a Peltier effect element with N doping and a Peltier effect element with P doping respectively. The invention further relates to an endoscope comprising at least one such structure.

20 Claims, 3 Drawing Sheets

LONGITUDINALLY-STEERABLE STRUCTURE AND ENDOSCOPE COMPRISING SAID STRUCTURE

BACKGROUND OF THE INVENTION (1) Field of the Invention

The present invention relates to an orientable longitudinal structure and to its method of manufacture, said structure comprising substantially longitudinal actuators made of shaped memory alloy (SMA), n-doped and p-doped Peltier elements and electrical operating means.

Such a structure is intended in particular for endoscopes, whether these be used in the medical field or in industry.

(2) Prior Art

Endoscopes are optical systems allowing inaccessible areas to be explored visually. They comprise, in particular, a flexible body of variable length intended to be introduced into the area that is to be inspected and on the end of which a viewing system is mounted. The end of the head of the endoscope is articulated so that the viewing system can be pointed in several directions, thus allowing the region that is to be inspected to be seen.

The prior art already discloses numerous solutions for orientating the heads of endoscopes.

Apart from the conventional mechanical control systems that use steel cables connecting the head of the endoscope to the operator's control member, the prior art also discloses solutions based in particular on the use of shaped memory alloys.

U.S. Pat. No. 5,624,380 proposes a manipulator with several degrees of freedom exhibiting a plurality of flexible parts that can be flexed selectively.

Said manipulator consists of a flexible tube comprising:
a plurality of flexible parts arranged in rows,
a plurality of SMA actuators,
power transmission means (such as conducting wires) for transmitting power to the actuators, running along the flexible tube,
power supplying elements arranged in series between said power transmission means and said actuators so as to control the energy supplied to the actuators by said power transmission means.

According to one embodiment of the invention, the manipulator comprises a plurality of substantially cylindrical flexible parts arranged in an axial direction. A pair of thermally deformable elements, each consisting of a leaf of SMA, is arranged between the front flexible parts and the adjacent rear flexible parts in order to curve said flexible parts.

Japanese patent application JP200135288 also discloses a cylindrical mobile element for an endoscope or catheter, it being possible for said cylindrical element to be flexed or turned in a required direction with a rapid response rate.

To do this, said cylindrical element comprises a plurality of elements made of SMA and p-doped and n-doped Peltier elements. These elements are arranged alternately and held between plastic rings exhibiting a central cavity.

The p-doped and n-doped Peltier elements are connected in series by electrodes such that the heat-generating parts and the heat-absorbing parts are in the same position. The elements are curved in a required direction by the selective application of current to the Peltier elements.

The systems described hereinabove do, however, present numerous disadvantages.

As far as the conventional mechanical systems are concerned, these have the disadvantage of generating significant friction between the control cables and the endoscope sheath, thereby limiting the useful exploration length.

Furthermore, local control of each articulation is impossible, thereby generating a risk of contact with certain areas of the environment explored, which risks are particularly damaging in the case of medical functional explorations.

As far as the systems developed in the Japanese patent application or the American patent which are cited hereinabove are concerned, these also present certain disadvantages.

In particular, the SMA actuators used are generally in the form of wires. Now, such wires exhibit relatively restricted elongation as a function of temperature. In order to obtain actuators that produce sufficient movement it is then necessary to have relatively long wires.

Furthermore, such systems display the disadvantage of leading to endoscopes that are relatively bulky because of the nature of the actuators and their positionings in the endoscope. Such actuators effectively generally limit the internal space of the endoscope or increase the outside diameter thereof.

SUMMARY OF THE INVENTION

The present invention intends to remedy the disadvantages of the prior art by proposing an orientable structure, operating from a simple electrical control, and making it possible to obtain endoscopes comprising a limited number of parts needed for operation and a greatly reduced diameter so as to form low-bulk endoscopes while at the same time guaranteeing good resolution in the positioning of the head.

To do this, the present invention is of the type described hereinabove and is notable, in its broadest acceptation, in that said actuators are arranged in pairs and positioned antagonistically, each actuator being in contact substantially at its ends with an n-doped Peltier element and a p-doped Peltier element respectively.

As a preference, said actuators are leaves, preferably one-piece leaves.

The actuators are preferably assembled with the Peltier elements by welding.

Advantageously, each n-doped and p-doped Peltier element is in contact with a partially annular conducting element which is preferably made of copper. Contact is preferably achieved through welding.

Advantageously, said actuators, associated with the Peltier elements, are positioned diametrically opposite each other with respect to the longitudinal axis of the structure.

Advantageously, said actuators are made of nickel titanium (NiTi) alloy, and said Peltier elements are made of bismuth telluride.

Said structure further comprises epoxy resin covering said Peltier elements including the thermoelectric junctions with said actuators, this being with a view to strengthening said Peltier elements.

The present invention also relates to an endoscope comprising a longitudinal body having, at its distal end, a viewing system, characterized in that at least part of the longitudinal body is formed using at least one orientable longitudinal structure described hereinabove.

As a preference, at least part of the longitudinal body of said endoscope is formed of a plurality of orientable longitudinal structures, said structures being stacked on top of one another in such a way that the conducting element of one of said structures bearing the n-doped elements is adjacent to the conducting element bearing the p-doped Peltier elements of the previous structure.

Advantageously, the actuators of at least one structure present, with the actuators of a previous and/or next structure, deformations in different directions.

The present invention also relates to the method of manufacturing an orientable longitudinal structure such as described hereinabove and in which the SMA activators are leaves. Said method comprises, in succession:
- a step of preparing SMA actuators consisting in cutting leaves presenting a curved shape from a sheet of SMA, preferably made of NiTi, said curved shape of the leaves corresponding to a "memorized" shape;
- a step of cooling said leaves until substantially straight leaves are obtained;
- a step of assembling said leaves obtained during the previous step with said Peltier elements, said assembly step consisting in incorporating said leaves between said n-doped and p-doped Peltier elements.

Said manufacturing method further requires a step of assembling said Peltier elements with annular conducting elements, preferably made of copper, and a step of pouring resin to cover said Peltier elements, including the thermoelectric junctions with said actuators.

As a preference, the step of assembling said leaves and said conducting elements with said Peltier elements consists in a welding operation.

BRIEF DESCRIPTION OF THE DRAWINGS

The invention will be better understood with the aid of the description given hereinafter by way purely of explanation, of one embodiment of the invention, with reference to the attached figures.

DETAILED DESCRIPTION OF THE PREFERRED EMBODIMENT(S)

Figure 1:
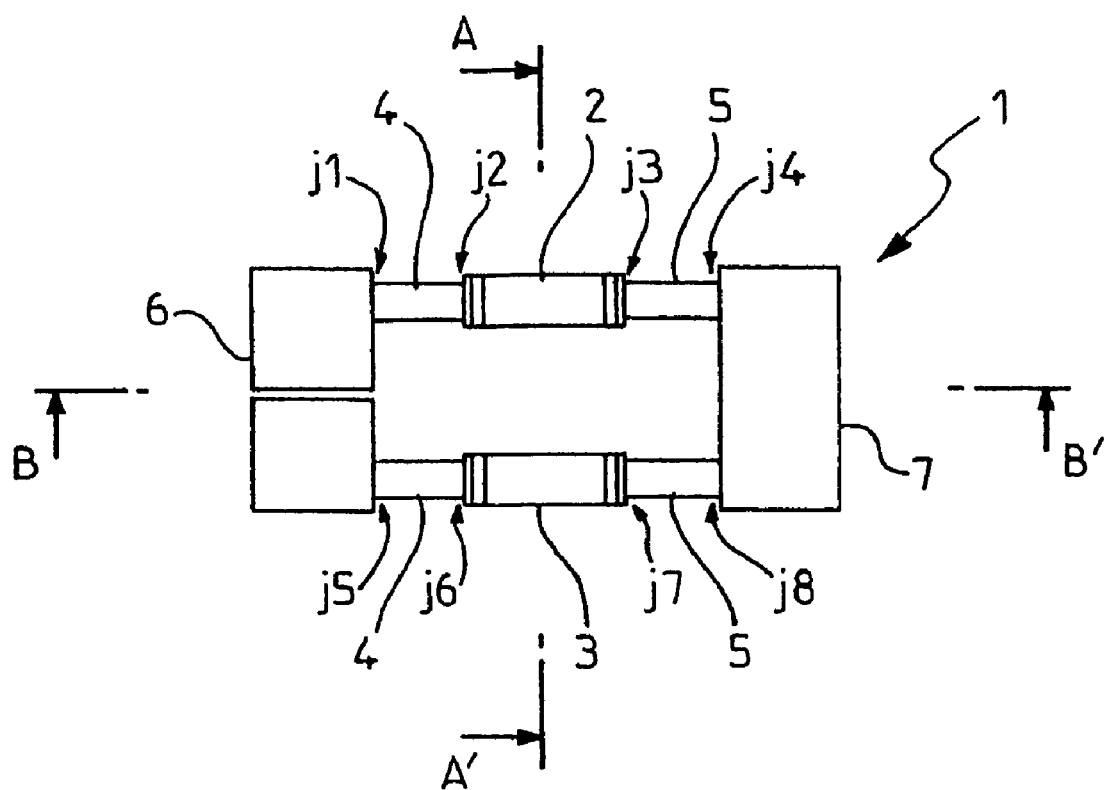
FIG. 1 illustrates a view from above of a longitudinal structure according to the invention.

The orientable longitudinal structure (1) according to the invention, illustrated in FIG. 1, comprises two leaves (2, 3) made of shaped memory alloy (SMA).

Said leaves (2, 3) made of SMA are arranged respectively between n-doped (4) and p-doped (5) Peltier elements so that the ends of each leaf (2, 3) are in contact respectively with one of the ends of an n-doped Peltier element (4) and one of the ends of a p-doped Peltier element (5).

Two annular conducting elements (6, 7) are arranged respectively one on each side of the free ends of said n- and p-doped elements (4, 5).

Figure 5:
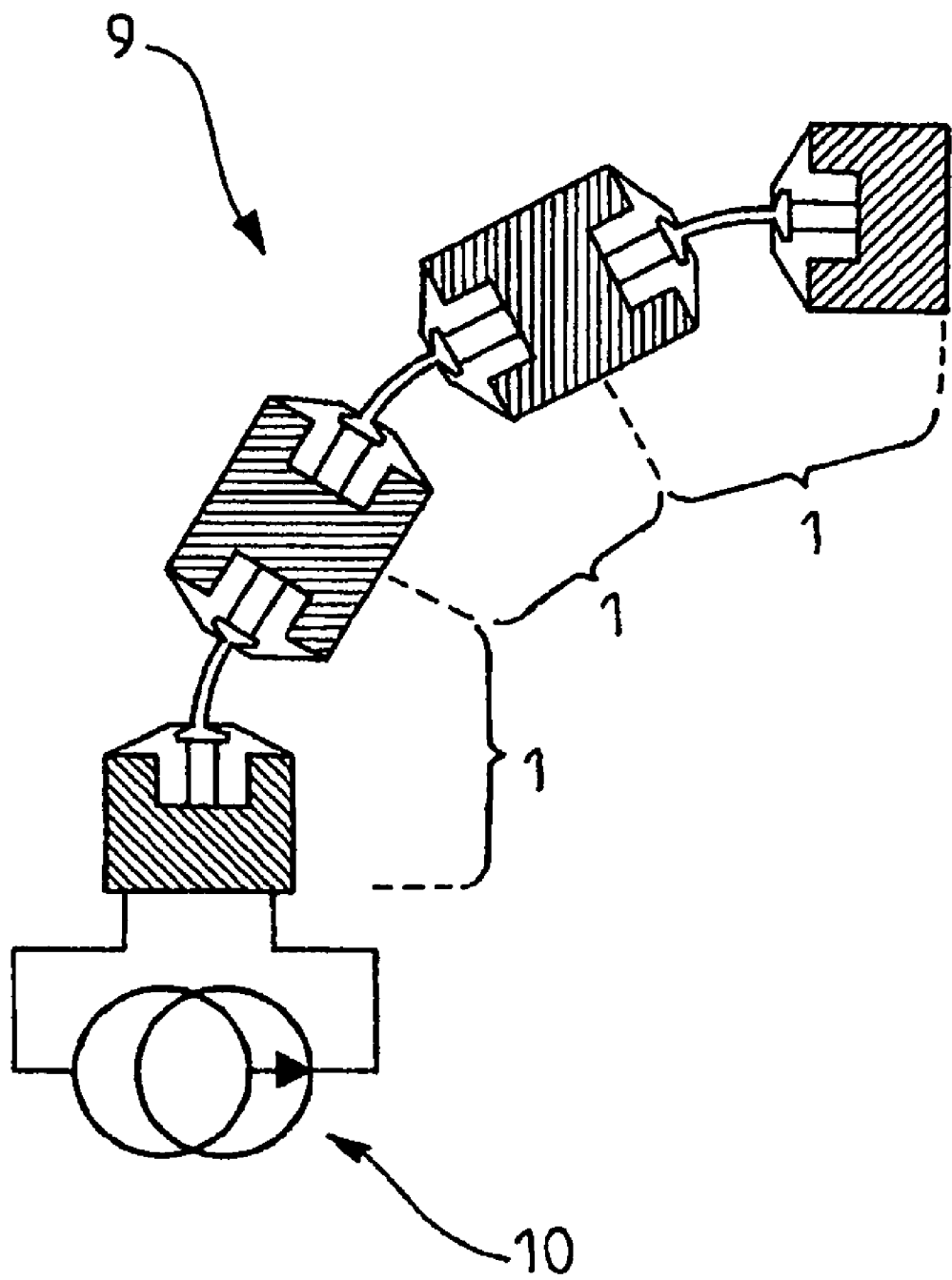
FIG. 5 illustrates a schematic view of a longitudinal body of an endoscope formed of a stack of structures according to the invention.

For a correct distribution of electrical current, the annular elements (6, 7) are preferably split into two electrically insulated annular half-elements. FIG. 1 depicts a structure (1) comprising two annular half-elements (6) and one annular element (7). For other applications, particularly involving the stacking of a plurality of structures (1) as depicted in FIG. 5, said structure will preferably comprises four annular half-elements (6, 7).

A thermoelectric circuit formed of a stack of the first conducting element (6) placed in contact with two n-doped Peltier elements (4), which are fixed respectively to one of the ends of one of said leaves (2, 3), the other end of said leaves (2, 3) being connected respectively to the two p-doped Peltier elements (5), also in contact with the second conducting element (7), is thus obtained.

Figure 2:
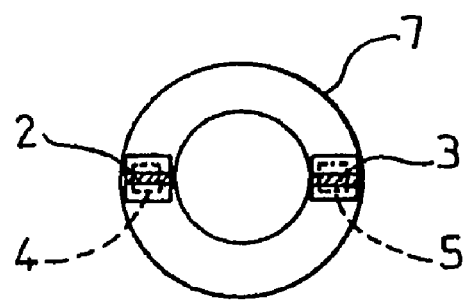
FIG. 2 illustrates a view in section on AA' of the structure of FIG. 1.

As a preference, said leaves (2, 3) associated with the Peltier elements (4, 5) are positioned diametrically opposite each other with respect to the longitudinal axis of said structure (1) as illustrated in FIG. 2.

Advantageously, said SMA leaves (2, 3) are one-piece leaves based on nickel titanium alloy.

Advantageously, said Peltier elements (4, 5) are made of bismuth telluride (BiTe), and said conducting elements (6, 7) of copper.

Although not depicted in FIG. 1, said structure (1) is connected to electrical operating means, of the current generator (10) type, as illustrated in FIG. 5.

The principle of manufacture of the structure (1) according to the invention is as follows.

The leaves (2, 3) are cut either at high temperature T, or at ambient temperature Ta after stress free cooling, from a sheet of NiTi with a curved shape. The initial shape of these leaves (2, 3) corresponds to a "memorized" shape. Thus, if the temperature is reduced down to ambient temperature Ta, it is possible to twist said leaves (2, 3) until a curvature the inverse of the curvature relating to the memorized shape is obtained. In order to return said leaves (2, 3) to their memorized shape, they need merely to be heated up to the temperature T again.

Figure 3:
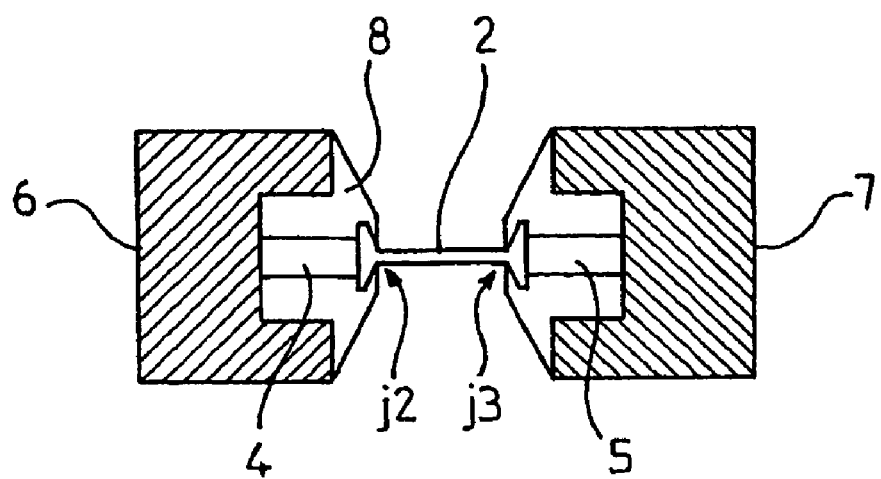
FIG. 3 illustrates a view in section on BB' of the structure of FIG. 1.

Once cut, said leaves (2, 3) are cooled then deformed to obtain a substantially straight shape (cf. FIG. 3).

Said leaves (2, 3), thus twisted to obtain substantially straight shapes, are then coupled to the Peltier elements (4, 5) thus producing thermoelectric junctions (j2, j3, j6, j7). More specifically, each leaf (2, 3) is incorporated between an n-doped Peltier element (4) and a p-doped Peltier element (5), taking care to mount said leaves (2, 3) in opposition with respect to their respective memorized shape. Thus, for a fixed direction of electrical current, the operator will direct said structure (1) in the desired direction: one of the leaves (the heating one) (2, 3) will cause the module to flex by virtue of the memory effect while the other (the cooling one) (3, 2) will undergo deformation in the opposite direction to its memorized shape.

Before that, the manufacture of said structure (1) involves a step of assembling said Peltier elements (4, 5) with said conducting elements (6, 7), thus producing thermoelectric junctions (j1, j4, j5, j8).

The structure (1) obtained thus forms a thermoelectric circuit which converts the electrical energy transmitted by said electrical operating means into thermal energy which is then imparted to said leaves (2, 3). As said leaves (1, 2) form an integral part of the thermoelectric conversion system, they therefore convert the thermal energy received into mechanical power, causing the flexing movement of the structure (1).

FIG. 3 illustrates a view of said structure (1) in section on BB' of FIG. 1.

Figure 4:
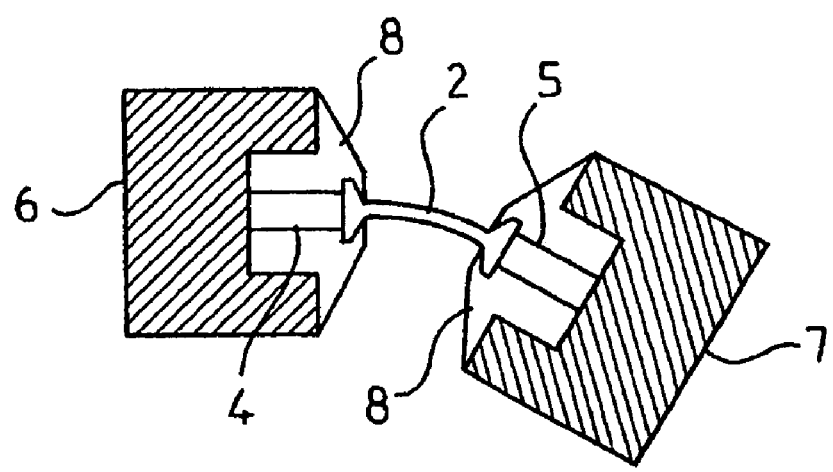
FIG. 4 illustrates a view in section on BB' of the structure of FIG. 1, said structure displaying a flexing movement.

This figure depicts the structure (1) comprising, on a part, some epoxy resin (8). This resin (8) is intended to strengthen said Peltier elements (4, 5) and the thermoelectric junctions (j1 to j8) that make up said structure (1). Specifically, the flexing movement is transmitted, as illustrated by FIG. 4, between the SMA leaves (2, 3) and the conducting elements (6, 7), said Peltier elements (4, 5) therefore experiencing significant loading. The addition of epoxy resin therefore allows said Peltier elements (4, 5) to be strengthened.

By using said electrical operating means to which said structure (1) is connected, a current is transmitted into the thermoelectric circuit, and supplies thermal power to said leaves (2, 3) which, in response, cause said structure (1) to effect a flexing movement (FIG. 4).

The flexing movement will be in one direction or another according to whether the current applied to said structure (1) is positive or negative. Thus, when a positive (or negative) current is applied to said structure (1), one of the leaves will cool down (or heat up), experiencing flexing in the opposite direction to its memorized shape (or flexing toward its memorized shape), while the other leaf will heat up (or cool down), then experiencing flexing toward its memorized shape (or flexing away from its memorized shape).

As said leaves (2, 3) were positioned between said Peltier elements (4, 5) during the assembly step so as to experience opposed deformations in the same direction, the leaf (2, 3) which, for a fixed direction of current, heats up, will cause said structure (1) to flex, by virtue of the memory effect, while the other leaf (3, 2), which in consequence cools down, experiences a deformation of the martensite reorientation type. The direction of flexing of said structure (1) is therefore dictated by the leaf (2, 3) which heats up and acts as a "master leaf", the second leaf (3, 2) acting as a "slave leaf".

FIG. 5 illustrates a schematic view of a longitudinal body (9) of an endoscope formed for example of a stack of three orientable longitudinal structures (1), each of said structures being identical and simply electrically connected to the previous one or the next one with a possibility of orientation about the longitudinal axis.

The stack is produced in such a way that the conducting element (6) of said structure (1) bearing the n-doped elements is adjacent to the conducting element (7) bearing the p-doped Peltier elements of the previous structure.

In one advantageous embodiment of the invention, the SMA leaves of a first structure (1) display, with the SMA leaves of a previous and/or next second structure (1), deformations in different directions.

Of course, the SMA leaves of one structure (1) may display, with the SMA leaves of another, previous and/or next, structure (1), deformations in identical directions.

The invention is described in the foregoing by way of example. It must be clearly understood that the person skilled in the art is capable of producing various variants of the invention without in any way departing from the scope of the patent.

The invention claimed is:

1. An orientable longitudinal structure comprising:
    an assembly of substantially longitudinal actuators made of shaped memory alloy;
    n-doped and p-doped Peltier elements, and electric control means;
    said actuators being arranged in pairs and positioned in parallel in an antagonist way opposite to each other with respect to their respective memorized shape;
    each said actuator being in contact substantially at its ends with an n-doped Peltier element and a p-doped Peltier element, respectively;
    each said n-doped Peltier element being in contact with a first at least partially annular conducting element and each said p-doped Peltier element being in contact with a second at least partial annular conducting element;
    the assembly being mounted in series with the electric control means to form a thermoelectric circuit so that, for a fixed direction of an applied current, one of the actuators of each said pair will heat and will undergo a flexion towards its memorized shape, and the actuator positioned in the antagonist way will cool and undergo a flexion opposite its memorized shape, and
    flexing movement of said structure being transmitted between said actuators and said conducting elements.

2. The orientable longitudinal structure as claimed in claim 1, wherein said actuators are leaves.

3. The orientable longitudinal structure as claimed in claim 2, wherein said leaves are one-piece leaves.

4. The orientable longitudinal structure as claimed in claim 1, wherein said conducting element is made of copper.

5. The orientable longitudinal structure as claimed in claim 1, wherein each said n-doped and p-doped Peltier element is welded to said conducting element.

6. The orientable longitudinal structure as claimed in claim 1, wherein said actuators, associated with the Peltier elements, are positioned diametrically opposite each other with respect to a longitudinal axis of the structure.

7. The orientable longitudinal structure as claimed in claim 1, wherein said actuators are welded to said n-doped and p-doped Peltier elements.

8. The orientable longitudinal structure as claimed in claim 1, wherein said actuators are made of nickel titanium (NiTi) alloy.

9. The orientable longitudinal structure as claimed in claim 1, wherein said Peltier elements are made of bismuth telluride.

10. The orientable longitudinal structure as claimed in claim 1, further comprising epoxy resin covering said Peltier elements including thermoelectric junctions with said actuators.

11. An endoscope comprising a longitudinal body having, at its distal end, a viewing system, wherein at least part of the longitudinal body is formed using at least one orientable longitudinal structure as claimed in claim 1.

12. The endoscope as claimed in claim 11, wherein at least part of the longitudinal body is formed of a plurality of said orientable structures, said orientable structures being stacked on top of one another in such a way that a conducting element of one of said orientable structures bearing the n-doped elements is adjacent to a conducting element bearing the p-doped Peltier elements of an adjacent orientable structure.

13. The endoscope as claimed in claim 11, wherein the actuators of at least one orientable structure present, with the actuators of another orientable structure, deform in different directions.

14. A method of manufacturing an orientable longitudinal structure as claimed in claim 2, wherein said method comprises, in succession:
    preparing SMA actuators consisting in cutting leaves presenting a curved shape from a sheet of SMA, said curved shape of the leaves corresponding to a "memorized" shape;
    cooling said leaves until substantially straight leaves are obtained; and
    assembling said leaves obtained during the previous step with said Peltier elements, said assembly step consisting in incorporating said leaves between said n-doped and p-doped Peltier elements.

15. The manufacturing method of claim 14, wherein said cutting step comprises cutting said leaves from a sheet of SMA made of NiTi.

16. The manufacturing method as claimed in claim 14, further comprising assembling said Peltier elements with partially annular conducting elements.

17. The manufacturing method as claimed in claim 14, wherein the assembly steps comprising welding said leaves to said Peltier elements.

18. The manufacturing method as claimed in claim 14, further comprising pouring resin to cover said Peltier elements, including thermoelectric junctions with said actuators.

19. A stack of orientable longitudinal structures comprising:
- a plurality of longitudinal structures,
- each said longitudinal structure being an orientable longitudinal structure comprising an assembly of substantially longitudinal actuators made of shaped memory alloy, n-doped and p-doped Peltier elements, and electric control means,
- said actuators being arranged in pairs and positioned in parallel in an antagonist way opposite to each other with respect to their respective memorized shape,
- each said actuator being in contact substantially at its ends with an n-doped Peltier element and a p-doped Peltier element, respectively,
- each said n-doped Peltier element being in contact with a first at least partially annular conducting element and each said p-doped Peltier element being in contact with a second at least partial annular conducting element;
- the assembly being mounted in series with the electric control means to form a thermoelectric circuit so that, for a fixed direction of an applied current, one of the actuators of each said pair will heat and will undergo a flexion towards its memorized shape, and the actuator positioned in the antagonist way will cool and undergo a flexion opposite its memorized shape, and
- each of said longitudinal structures being identical and electrically connected to a previous one of said longitudinal structures or to a next one of said longitudinal structures with a possibility of orientation about a longitudinal axis of said stack,
- wherein flexing movement of said structure is transmitted between said actuators and said conducting elements.

20. A stack of orientable longitudinal structures according to claim 19, wherein a conducting element of a structure bearing the n-doped elements is adjacent to a conducting element bearing the p-doped Peltier elements of the previous one of said longitudinal structures.

* * * * *